United States Patent
Stanbridge et al.

(10) Patent No.: US 10,004,775 B2
(45) Date of Patent: Jun. 26, 2018

(54) INHIBITION OF HYPOXIA-INDUCIBLE FACTOR ACTIVITY WITH CARICA PAPAYA EXTRACTS

(71) Applicants: The Regents of the University of California, Oakland, CA (US); Universiti Putra Malaysia, Selangor Darul Ehsan (MY)

(72) Inventors: Eric J. Stanbridge, Irvine, CA (US); Norazizah Shafee, Selangor (MY); Khatijah Yusoff, Selangor (MY)

(73) Assignees: The Regents of the University of California, Oakland, CA (US); Universiti Putra Malaysia, Selangor Darul Ehsan (MY)

( * ) Notice: Subject to any disclaimer, the term of this patent is extended or adjusted under 35 U.S.C. 154(b) by 24 days.

(21) Appl. No.: 15/279,999

(22) Filed: Sep. 29, 2016

(65) Prior Publication Data

US 2017/0014460 A1    Jan. 19, 2017

Related U.S. Application Data

(62) Division of application No. 14/208,524, filed on Mar. 13, 2014.

(60) Provisional application No. 61/784,150, filed on Mar. 14, 2013.

(51) Int. Cl.
    *A61K 36/185* (2006.01)
    *A61K 33/24* (2006.01)
    *A61K 31/549* (2006.01)

(52) U.S. Cl.
    CPC .......... *A61K 36/185* (2013.01); *A61K 31/549* (2013.01); *A61K 33/24* (2013.01); *A61K 2236/00* (2013.01); *A61K 2236/33* (2013.01)

(58) Field of Classification Search
    CPC .................................... A61K 36/185
    USPC .................................... 424/725, 774
    See application file for complete search history.

(56) References Cited

U.S. PATENT DOCUMENTS

| | | | | |
|---|---|---|---|---|
| 3,274,072 A | * | 9/1966 | Burdick | A61K 36/185 435/219 |
| 3,274,073 A | * | 9/1966 | Burdick | A61K 36/185 435/219 |
| 2008/0069907 A1 | * | 3/2008 | Morimoto | A23L 33/105 424/725 |
| 2010/0292264 A1 | * | 11/2010 | Zhu | A61K 31/4375 514/279 |

OTHER PUBLICATIONS

Runnie et al. J. Ethnopharmacol. 2004. vol. 92, pp. 311-316.*
Liew et al. J. Ethnophamacol. Sep. 2012. vol. 144, pp. 453-456.*
Baskaran et al. Asian Pacific J. Tropical Dis. 2012. pp. S658-S662.*
Imaga et al. J. Pharmacognosy Phytother. 2010. vol. 2(7), pp. 97-102.*

* cited by examiner

*Primary Examiner* — Christopher R Tate
(74) *Attorney, Agent, or Firm* — Berliner & Associates

(57) ABSTRACT

An extract of *Carica papaya* leaves obtained from a plant of age six months and younger from the date of germination of the seed is used as an inhibitor of HIF to effectively block hypoxia-inducible factor (HIF) function and methods of use thereof. More specifically it relates to the use of the *Carica papaya* plant extract to eliminate unwanted cells by inhibiting HIF in the prevention and treatment of hypoxia-related conditions and diseases such as inflammatory diseases, vascular diseases, cancer and infectious diseases. In a particular embodiment, a solid hypoxic tumor in a patient is treated by administering to the patient a therapeutically acceptable amount of an extract of *Carica papaya* leaves obtained from a plant of age six months and younger from the date of germination of the seed, preferably an alcohol extract such as a methanol extract, whereby to inhibit hypoxia-inducible factors in the tumor.

6 Claims, 4 Drawing Sheets

INHIBITION OF HYPOXIA-INDUCIBLE FACTOR ACTIVITY WITH CARICA PAPAYA EXTRACTS

This application is a divisional application of U.S. Ser. No. 14/208,524 filed Mar. 13, 2014 which claims the benefit of Provisional Patent Application No. 61/784,150, filed Mar. 14, 2013

FIELD OF THE INVENTION

The invention relates to the inhibition of hypoxia-inducible factor activity.

BACKGROUND OF THE INVENTION

The use of plant extracts in Traditional Chinese Medicine (TCM) can be traced back to 6000 years ago (Solecki and Shanidar, 1975). In recent years, there has been a burgeoning use of plant extracts in TCM for modern drug discovery (Graziose et al., 2010). These plant extracts are used for a variety of purposes including health improvement, beauty, and nutritional supplementation, as well as prevention and treatment of diseases, including diabetes and cancer (Graziose et al., 2010).

*Carica papaya* one of the candidate plants. It has been reported to have medicinal properties towards various diseases including dengue fever (Ahmad et al., 2011), wound healing (Mahmood et al., 2005) and asthma (Canini et al., 2007). Extracts from *Carica papaya* were also claimed to have anti-cancer properties (Morimoto et al., US Patent Application No. 20080069907). These investigators, however, did not indicate the specific mechanisms that were involved in the anti-cancer effects, nor did they indicate that the age of the plant could have any effect on the efficacy of the treatment.

Oxygen homeostasis is a critical element for physiological well-being of the human body. Limited oxygen supply, termed hypoxia, plays a major role in the pathobiology of solid tumors. Hypoxia and oxidative stress pathways are associated with various human disorders, including inflammatory diseases, vascular diseases, cancer and infectious diseases. Cells in hypoxic regions of tumors are more resistant to radiation and chemotherapy (Brown, 2000). They are also more resistant to cell death signaling (Seol et al., 2009). Master regulators of cell survival under hypoxia are the hypoxia-inducible factors (HIFs), HIF-1 and HIF-2. These transcription factors regulate several processes vital for the cells to survive the hypoxic conditions (Semenza, 2011; Miyara et al. 2011). Since these cancer cells have altered metabolic mechanisms for survival under hypoxia, we conjectured that their responses to plant extracts also will be different from normoxic cancer cells. Even though HIF-inhibitory drugs have been approved by the US-FDA for clinical use (Xia et al., 2012), their undesirable side effects are still problematic (Sanchez et al., 2012; Yamaguchi et al., 2012). Due to the limited number of drug candidates in the pipeline and the adverse side effects of the approved ones, identification and development of candidate drug inhibitors that target the HIF-1 pathway are urgently needed.

BRIEF SUMMARY OF THE INVENTION

We have discovered that methanolic extracts of certain *Carica papaya* leaves have a potent inhibitory effect on HIF. The *Carica papaya* leaves effective in this invention are "young" leaves, which in this invention is defined as obtained from a plant of age six months and younger from the date of germination of the seed, i.e., six months and younger from the date the plant seed sprouts. Cytotoxicity analyses showed that such young *Carica papaya* extracts caused high toxicity towards hypoxic cells but not normoxic cells. This specificity is crucial when one targets to eliminate only the hypoxic cells. Based on this specificity, adverse side effects of the extracts and their general toxicity on non-target cells will potentially be eliminated. Therefore, in accordance with this invention, an extract of young *Carica papaya* leaves is used as an inhibitor of HIF to effectively block hypoxia-inducible factor (HIF) function and methods of use thereof. More specifically it relates to the use of such young *Carica papaya* plant extract to eliminate unwanted cells by inhibiting HIF. The compounds and compositions of the present invention are useful in the prevention and treatment of hypoxia-related conditions and diseases such as inflammatory diseases, vascular diseases, cancer and infectious diseases.

In a particular embodiment, a method is provided for treating a solid hypoxic tumor in a patient, comprising the steps of identifying a patient having a solid hypoxic tumor, and administering to the patient an extract of young *Carica papaya* leaves. The extract can be administered to the patient as a therapeutically acceptable amount of a pharmacon comprising the extract in a pharmaceutically acceptable carrier wherein the patient is not otherwise indicated for treatment with the extract of *Carica papaya* leaves. The pharmacon can be formulated as a liposome, incorporated into a polymer release system, or suspended in a liquid in a dissolved form or as a colloidal form.

In another embodiment, the extract is administered in combination with a chemotherapeutic agent, such as cisplatin or chetomin.

In another embodiment of the invention, we provide as a composition of matter an alcohol extraction from young *Carica papaya* leaves.

In another embodiment of the invention, we provide an article of manufacture comprising a vessel containing an extract of young *Carica papaya* leaves and instructions for use of the extract for the treatment of a solid hypoxic tumor in a method comprising identifying a patient having a solid hypoxic tumor, and administering to the patient an effective amount of an extract of young *Carica papaya* leaves. An effective amount of a composition for treating a cancer will be that amount necessary to inhibit mammalian cancer cell proliferation in situ. Those of ordinary skill in the art are well-schooled in the art of evaluating effective amounts of anti-cancer agents.

In another embodiment of the invention, we provide an article of manufacture comprising packaging material and contained within the packaging material, an extract of young *Carica papaya* leaves wherein the packaging material comprises a label that indicates that the extract can be used for treating a solid hypoxic tumor In a further embodiment of the invention, the young *Carica papaya* leaves are extracted with an alcohol, which can be monohydric, polyhydric, unsaturated aliphatic, or alicyclic

BRIEF DESCRIPTION OF THE DRAWINGS

For a more complete understanding of the present invention, reference is now made to the following descriptions taken in conjunction with the accompanying drawing, in which.

DETAILED DESCRIPTION OF THE INVENTION

Figure 1A:
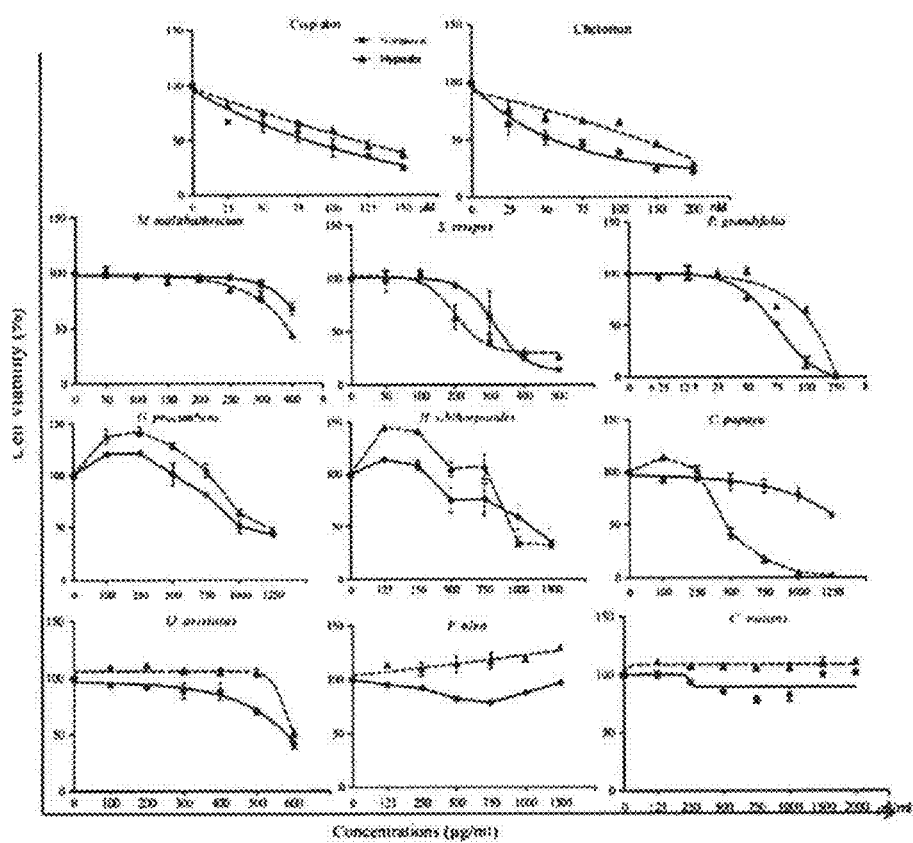
FIG. 1A shows the effects of methanolic plant extracts on Saos-2 cells in normoxia and hypoxia with dose response curves from an MTT assay and where cisplatin and chetomin were used as positive controls.
Figure 1B:
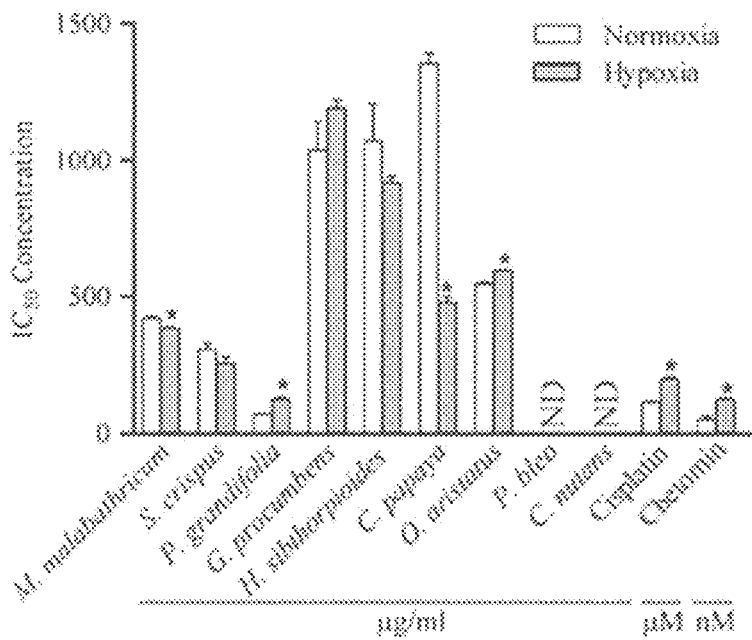
FIG. 1B shows a compilation of the $IC_{50}$'s of the extracts and experimental control drugs in which data are shown as mean±S.E.M. of triplicates from a representative of three independent experiments, and in which the asterisk (*) represents a significant difference (P<0.05) among the $IC_{50}$ in normoxia and hypoxia.

The discovery of the unique properties of the extract of young Carica papaya leaves arose from an investigation of the effects of the extracts of various plants on HIF activity, and the effect of the age of the Carica papaya leaves on HIF inhibitory activities. Descriptions of those experiments will be given followed by specific investigations of extracts from Carica papaya leaves.

The Effects of the Extracts of Various Plants on HIP Activity

Cell Line and Culture Conditions

A human osteosarcoma cell line, Saos-2 stably expressing four copies of the erythropoietin hypoxia response elements (HRE-luc Saos2; Shafee et al., Malaysian Patent Application #: PI 2012003492), was cultured in DMEM medium (PAA, USA) supplemented with 10% (v/v) fetal bovine serum (FBS; PAA, USA) and 1% (v/v) antibiotic-antimycotic (PAA, USA) in a humidified incubator supplied with ambient oxygen and 5% $CO_2$ at 37° C. An hypoxic gaseous environment was created by incubating cells in a ProOx in vitro chamber (BioSpherix), controlled by ProOx model 110 (BioSpherix). The cells were supplied 0.5% $O_2$, 94.5% $N_2$ and 5% $CO_2$ at 37° C.

Plant Materials, Cell Culture Treatment and Viability Assay

Nine types of plants with known medicinal properties were tested in this study, and are described in Table 1:

TABLE 1

Plants used in the study and their medicinal uses.

| Plant name | Medicinal use and references |
| --- | --- |
| Melastomataceae<br>Melastoma<br>malabathricum<br>L. | Anti diarrhoeal (Sunilson et al., 2009), antimicrobial (Thatoi et al., 2008), cytotoxicity, antiviral (Lohezic Le Devehat et al., 2002), anticoagulant (Manicam et al., 2010), antipyretic, anti-inflammatory, antinociceptive (Zakaria et al., 2006), antioxidant, free radical scavenging activity and anticancer (Susanti et al., 2007). |
| Acanthaceae<br>Strobilanthes<br>crispa<br>T. Anderson | Antidiabetic, diuretic, antilytic, laxative (Sunarto, 1977), anticancer (Yaacob et al., 2010), anti-AIDS, antihypertensive (Liza et al, 2010), antioxidant (Abu et al., 2007), antihyperglycemic and antilipidemic (Fadzelly et al., 2006) |
| Cactaceae<br>Pereskia<br>grandifolia<br>Haw. | Antitumour, anti-rheumatic, antiulcer, anti-inflammatory (Goh, 2000), relief of headache, gastric pain, hemorrhoids, atopic dermatitis, body revitalization (Goh, 2002; Rahmat, 2004; Tan et al., 2005), reduce swelling (Sahu et al., 1974; Anon, 1969) and antioxidant (Sim et al., 2010). |
| Compositae<br>Gynura<br>procumbens<br>(Lour.) Merr. | Eruptive fever, rash, kidney disease, migraines, constipation, hypertension, diabetes mellitus, cancer (Perry, 1980), anti-herpes simplex virus, antidiabetic, urinary infection, antiallergic, reduce cholesterol and high blood pressure (Jiratchariyakul et al., 2000), antihyperglycaemic (Akowuah et al., 2001; Akowuah et al., 2002; Hassan et al., 2010), anti-inflammatory (Iskander et al., 2002; Jiratchariyakul et al., 2000), anti-hyperlipidaemic (Zhang and Tan, 2000), hypertension (Lam et al., 1998; Kim et al., 2006), wound healing (Zahra et al., 2011) and antiulcer (Mahmood et al., 2010), antioxidant and antitumour (Maw et al., 2011) |

TABLE 1-continued

Plants used in the study and their medicinal uses.

| Plant name | Medicinal use and references |
| --- | --- |
| Umbelliferae<br>*Hydrocotyle*<br>*sibthorpioides*<br>Lam. | Cancer (Yu et al., 2007; Huang et al., 2008), fever (Manandhar, 1993; Pfoze et al., 2012), edema, detoxication, throat pain, diuretic, psoriasis (Li, 1986), rheumatalgia, dysentery, whooping cough, jaundice (Srivastava et al., 2012), viral infection (Li, 2000; Wang 2000; Yu et al., 2007). |
| Caricaceae<br>*Carica*<br>*papaya*<br>L. | Anti-tumor (Otsuki et al., 2010), anti-Dengue fever (Ahmad et al., 2011), antisickling (Imaga et al., 2009), vasodilatatory, antioxidant, reduction of cardiovascular risks (Runnie et al., 2004), wound healing (Mahmood et al., 2005), asthma relieving, vermifuge, treatment of gastric problems, fever, amoebic dysentery (Canini et al., 2007). |
| Labiatae<br>*Orthosiphon*<br>*aristatus*<br>(Blume) Miq. | Antioxidant (Hsu et al., 2010), anti-inflammatory (Hsu et al., 2010); Nadia et al., 2012), kidney stones (Hsu et al., 2010), dysuria (Premgamone et al., 2008), hypertension (Matsubara et al., 1999; Ohashi et al., 2000). |
| Cactaceae<br>*Pereskia*<br>*bleo*<br>DC. | Anticancer (Malek et al., 2009; Tan et al., 2005), antitumour, anti-rheumatic, antiulcer, anti-inflammatory, antidiabetic and hypertension (Goh, 2000), antiproliferative and mutagenic (Er at al., 2007), relief of headache, gastric pain, hemorrhoids, atopic dermatitis, body revitalization (Goh, 2002; Rahmat, 2004; Tan et al., 2005). |
| Acanthaceae<br>*Clinacanthus*<br>*nutans*<br>(Burm. f.) Lindau | Skin rashes, insect and snake-bite, analgesic, anti-inflammatory (Satayavivadetal., 1996; Wanikiat et al., 2008), anti-HSV and anti-VZS (Jayavasu et al, 1992; Thawaranantha et al., 1992), bladder activity (Low et al., 2011). |

The voucher specimens were deposited in the Herbarium of Institute of Biosciences, Universiti Putra Malaysia. Leaves of these plants were subjected to methanolic extraction as described in Hsu et al., 2010. The leaves were washed with distilled water and left to air-dry at room temperature or in an oven at 40° C. until a constant weight was obtained. Dried leaves were then blended into a powder form, soaked and extracted in methanol at a 1:3 ratio (w/v) for three days at room temperature. Extracts were filtered by Whatman No. 1 filter paper with the aid of a vacuum pump. The residues were re-extracted twice using the same methanolic method. Filtrates were then concentrated by rotary evaporator at a maximum of 40° C. Concentrated extracts were collected in glass vials with push-in caps and dried in an oven at 40° C. until a constant weight was obtained. All of the crude extracts were stored −80° C. Prior to use, the extracts were prepared at the required concentrations by dissolving them in serum-free DMEM media with a final DMSO concentration of less than 0.5% (v/v), centrifuged at 1000×g and filtered through 0.22 µM filters. Overnight cultures of cells, initially seeded at $1.5 \times 10^4$ cells per well in a 96-well plate, were treated with selected concentrations of plant extracts and incubated in normoxic or hypoxic conditions. After 24 h of incubation, an MTT assay (Jamal et al., 2012) was employed to determine cell viability following treatment of cultured cells with selected concentrations of the crude plant extract. These concentrations were determined empirically and selected to cover a range of effects, ranging from no effect to significant cytotoxicity. Initially, cells were seeded at $1.5 \times 10^4$ cells per well in a 96-well plate for 24 h. The cells were treated with selected concentrations of the extract and incubated in normoxic or hypoxic conditions. After 24 h of treatment, spent culture medium was replaced with fresh serum-free DMEM containing 0.5 mg/ml MTT. After a further 4 h of incubation in 5% $CO_2$ at 37° C., formazan precipitates that formed were dissolved with 100 µl of DMSO and the reaction was read in a microplate reader (Model 550, BioRad, Hercules, Calif.) at 570 nm absorbance and 630 nm as the reference wavelength.

HIF Reporter Assay

Cells were co-transfected with a hypoxia-driven firefly luciferase reporter plasmid construct containing four copies of the erythropoietin (EPO) hypoxia response elements (HRE) and a pRL-CMV expressing *Renilla* luciferase as described previously (Kaluz et al., 2008, Shafee et al., 2009, Shafee et al. Malaysian Patent Application No. PI 2012003492). Transfected cells were treated with appropriate concentrations of plant extracts and incubated in either normoxic or hypoxic conditions. After 24 h, firefly and *Renilla* luciferase signal intensities were measured (Kaluz et al., 2008, Shafee et al, 2009). Percent HIF inhibition was calculated as a ratio of the difference between untreated and plant extract-treated sample to the untreated sample. A positive value indicates HIF inhibition, while a negative value denotes HIF activation.

Statistical Analysis

The Student t-test was used to analyze the experimental data in this study. Results were expressed as mean±standard error of the mean (SEM). A $p$ value of <0.05 was considered significant.

Results and Discussion

To investigate whether hypoxia affects cellular responses to plant extract treatment, cells were treated with selected concentrations of each extract, and their viability was determined. As positive controls for inhibition of HIF activity, we included cisplatin (Duyndam et al., 2007), and Chetomin (Tan et al., 2005). Different patterns of cytotoxicity were observed when the cells were treated in normoxic versus hypoxic conditions. As expected (Song et al., 2006), the $IC_{50}$ value for cisplatin in hypoxia is significantly higher than in normoxia (FIG. 1A). For the first time, we show that the $IC_{50}$ of chetomin also increased in hypoxia.

*Melastoma malabathricum*, *Strobilanthes crispus* and *Pereskia grandifolia*, showed no drastic differences in cytotoxicity when lower concentrations (<50 µg/ml) of extracts were used (FIG. 1A). However, at concentrations higher than 150 µg/ml, cytotoxicity to *Melastoma malabathricum* became more evident in the hypoxic compared to the normoxic cultures. Cytotoxic and antiproliferative activities of methanolic extracts of *Melastoma malabathricum* have been previously reported (Devehat et al., 2002). Their studies, which were done under normoxia, showed that the $IC_{50}$ values of the extract ranges from 19 to >400 µg/ml depending on the cell line tested. Results in the present study showed that hypoxic cancer cells are more susceptible to *Melastoma malabathricum* cytotoxicity when the concentrations used are above 150 µg/ml. Therefore, it is likely that the $IC_{50}$ of the extracts will be lower in hypoxic cancer cells. For *Strobilanthes crispus* the difference in cytotoxicity began to be seen as early as 100 µg/ml. Beginning at this concentration, cells in the hypoxic environment showed a higher rate of cell death compared to the cells in the normoxic environment. The opposite situation was observed in the cells treated with *Pereskia grandifolia*. Cytotoxicity of the cells was observed to be higher in the normoxic condition instead, even though cytotoxicity was seen earlier, at 25 µg/ml.

*Gynura procumbens, Hydrocotyle sibthorpioides* and *Carica papaya* extracts showed different cytotoxicities in normoxia and hypoxia at all concentrations used. *Gynura procumbent* and *Hydrocotyle sibthorpioides* were found to induce cell proliferation at concentrations lower than 150 µg/ml. No induction was seen for *Carica papaya* extract. Interestingly, in hypoxia, all these extracts induced higher cell proliferation than in normoxia. To the best of our knowledge, this is the first report to show induction of cell proliferation in cancer cells by these three plant extracts. *Gynura procumbens* has been shown to contribute towards the wound healing process (Zahra et al., 2011). Our findings of increased cell proliferation, albeit in cancer cells, may help contribute towards further understanding of mechanisms involve in the process of wound healing. Similar to our findings in the normoxic condition, the inefficiency of *Hydrocotyle sibthorpioides* extracts in cell killing was also reported previously (Huang et al., 2008). They showed that the $IC_{50}$ of *Hydrocotyle sibthorpioides* ethanolic extracts in cancer cells was >2000 µg/mL. For *Carica papaya*, we observed a minimal stimulatory effect in hypoxia at concentrations lower than 250 µg/ml. However, above this concentration, its cytotoxicity increased tremendously. In normoxia, on the other hand, the extract showed a gradual increase in cytotoxicity with increasing concentrations of extracts. This result is supported by Otsuki et al. (2010) which reported anti-proliferative responses of various tumor cell lines in normoxic conditions towards *Carica papaya* extracts.

*Orthosiphon aristatus, Pereskia bleo* and *Clinacanthus nutans* extracts showed minimal cytotoxicity in both normoxic and hypoxic conditions. *Orthosiphon aristatus* extract, which was previously shown to have antioxidant and anti-inflammatory effects (Hsu et al., 2010), showed a gradual reduction of cell viability with increasing amounts of extract used in the normoxic condition. But in the hypoxic condition, no statistically significant difference in cytotoxicity was observed until 500 µg/ml were used, when a sharp drop in cell viability was observed in both normoxic and hypoxic conditions, indicating a general cytotoxity. For *Pereskia bleo* and *Clinacanthus nutans* extracts, no significant cytotoxicity was seen until at the highest concentrations tested under normoxic conditions. This finding is in agreement with a study by Er et al. (2007) which also failed to observe any notable anti-proliferative effect of *Pereskia bleo* methanolic extract in 4T1 and NIH/3T3 cell lines. In contrast, Malek et al. (2009) reported cytotoxicity effects of *Pereskia bleo* methanolic extract in several cancer cell lines. Besides the different types of cancer cells used, another possible explanation for these inconsistencies is the gaseous conditions used in their studies. In our study, we found that hypoxic environment led to growth stimulatory response by *Pereskia bleo* but not for *Clinacanthus nutans*. This result strongly suggests that microenvironmental conditions contribute towards cellular responses to plant extract treatments. Specific Investigation of Extracts from *Carica papaya* Leaves.

Figure 3:
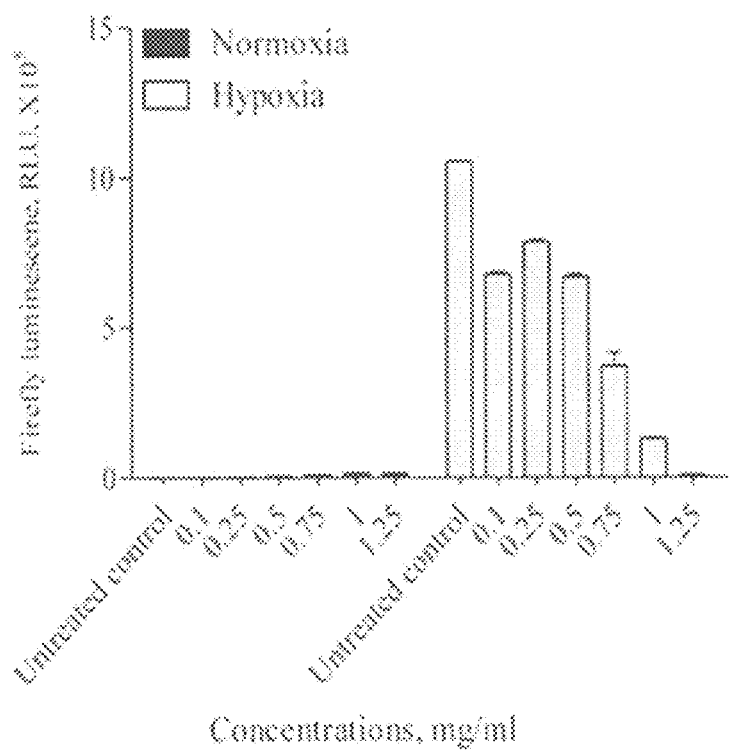
FIG. 3 shows the effects of Carica papaya extract treatment on HIF-driven reporter gene expression in which the HRE-luc Saos2 cells (Malaysian patent filing #: PI 2012003492) were treated with different concentrations of Carica papaya extract and incubated in either normoxic or hypoxic conditions, and in which Luciferase signal intensities were measured after 24 hours.

The following describes the specific investigation of whether HIF is affected by *Carica papaya* plant extract treatment, HRE-luc Saos2 cells were treated with selected concentrations of the extract, and their HIF-responsive luciferase signal was determined. The untreated samples showed the expected response pattern, where the signal was only increased in hypoxia but not normoxia (FIG. 3). The high hypoxic signal was dramatically reduced in cells treated with various concentrations of *Carica papaya* extracts. At the lowest concentration tested (0.1 mg/ml) the signal was reduced by almost 40%. As the concentration of the extract increased, the signal also decreased. However, due to the possibility of general cytotoxicity of the extracts on the cells, the reduced signals need to be further studied. Prior to performing further investigation, we compared the inhibitory properties of the *Carica papaya* against cisplatin, a known inhibitor of HIF (Duyndam et al., 2007).

Figure 4:
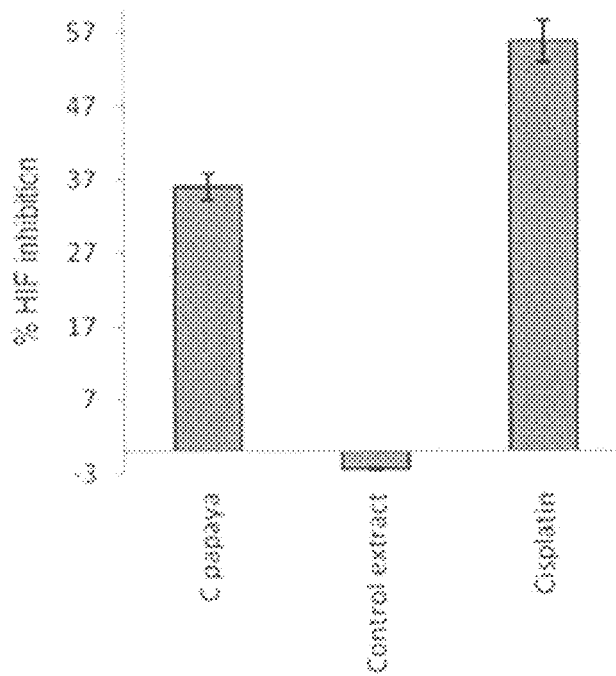
FIG. 4 shows the percent HIF inhibition in the plant extract or drug-treated hypoxic HRE-luc Saos2 cells where Carica papaya and control extract concentrations were 0.1 mg/ml., cisplatin concentration was 0.1 mM. The percent HIF inhibition was calculated as a ratio of the difference between untreated and treated sample to the untreated sample, and a positive value indicates HIF inhibition, while a negative value denotes HIF activation.

At 0.1 mg/ml concentration, *Carica papaya* extract reproducibly inhibits HIP signals by approximately 40% (FIG. 4). This inhibition was comparable to cisplatin, where the inhibition was around 60%. To confirm that the signal inhibition was not due to a general effect of extract treatment on the HRE-luc Saos2 cells, another plant extract was used as a control. Treatment of this extract at a similar concentration to *Carica papaya* extract, did not result in any HIF inhibitory signal. Instead, a slight increase was observed. This increase was expected since HIF is also a stress-response signal (Semenza, 2011; Miyata et al., 2011). Therefore, cells which undergo stress, in this case perhaps by the presence of the extract, will display a slight increase in HIF activity. These data clearly demonstrate the specificity of *Carica papaya* extract on HIF inhibition.

To verify that the reduced HIF signals were not due to cytotoxicity effects of the *Carica papaya* extract on the cells, we performed an MTT assay on the treated cells. At 0.1 mg/ml concentration, where HIF signal was suppressed by as much as 40%, the cells appeared to be viable (FIG. 1A). In fact, the cell number was slightly increased in the hypoxic condition, suggesting a minimal effect of the *Carica papaya* extract on the general properties of the cells. At higher concentrations, the extract began to affect cell viability, particularly in the hypoxic condition. This interesting observation suggests that hypoxic cells are more susceptible to *Carica papaya*-induced cytotoxicity compared to normoxic cells. Therefore, *Carica papaya* is an ideal candidate to eliminate unwanted hypoxic cells. To observe the pattern of HRE-luc Saos2 cell killing by HIF-inhibitors in normoxic and hypoxic conditions, cisplatin was used. Additionally, another specific inhibitor of HIF, chetomin (Tan et al., 2005), was also used. This was a proof-of-concept study to confirm the results observed in the *Carica papaya* extract-treated samples. Referring to the respective plots for *Carica papaya*, cisplatin, and chetomin in FIG. 1A, a different pattern of cytotoxicity was observed when the cells were treated with these drugs in normoxic versus hypoxic conditions. As expected, the $IC_{50}$ value for cisplatin in hypoxia is significantly higher than in normoxia. Hypoxia-induced resistance to cisplatin treatment was previously reported (Song et al., 2006). For the first time, we have shown in this study that the $IC_{50}$ of chetomin also increased in hypoxia. Overall Our data demonstrate that methanolic Carica papaya plant extracts showed different $IC_{50}$ values in hypoxic versus normoxic conditions (FIG. 4). This is not entirely unexpected, since cellular responses and adaptations to the hypoxic environment are complex and play important roles in normal cellular physiology. Hypoxic tumor cells are known to be more resistant to certain drugs (Reviewed in Brown, 2000). We found that the $IC_{50}$ of Carica papaya extract in hypoxia was reduced by almost 3-fold when compared to normoxia. This finding demonstrates Carica papaya as a candidate for the elimination of unwanted hypoxic cells. To investigate the effects of a combination treatment, using Carica papaya with either cisplatin or chetomin, we performed experiments using $IC_{50}$ concentrations of each material. Results obtained showed that the combination treatment led to an increase in cytotoxicity compared to individual treatments. In this combination treatment, the killing effect improved by 4-fold in both conditions tested. This observation suggests that Carica papaya is a good candidate, as individual or combination treatment for drug resistant cells, particularly with respect to targeting hypoxic cells.

Figure 2:
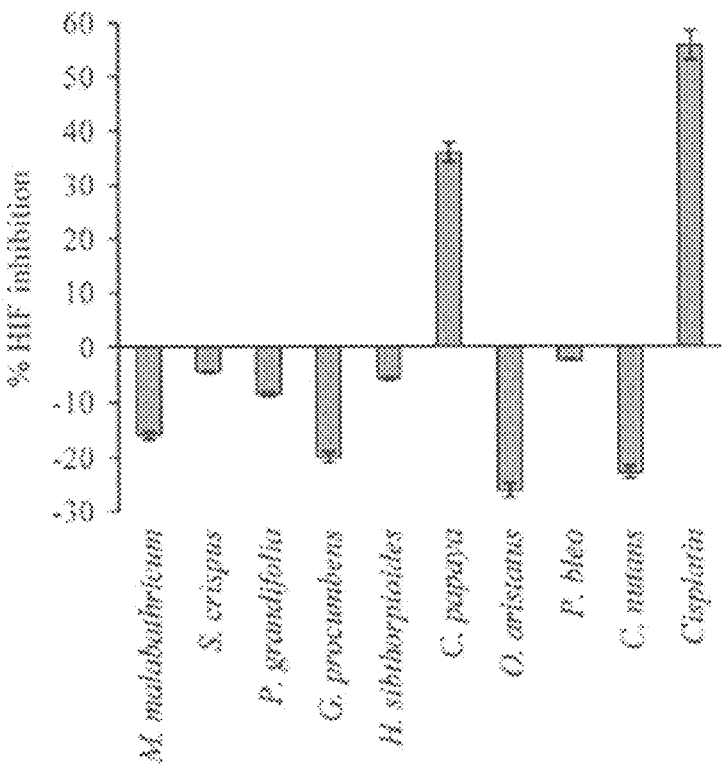
FIG. 2 shows the effects of plant extract treatment on HIP activities in hypoxic Saos-2 cells where a hypoxia driven firefly luciferase reporter assay was used to measure HIF activity in the cells and positive values indicate increased HIF inhibition while negative values showed HIF activation.

Since HIF is known to be a master regulator of cellular responses to low oxygen conditions (Semenza, 2011), it is likely that the variation in cellular responses to plant extracts in hypoxic versus normoxic conditions was due to differences in their HIP activities. To investigate this possibility, a hypoxia-driven reporter assay (Kaluz et al., 2008) was performed in samples treated with the lowest concentrations of each plant extract. Signal intensity of this assay is directly proportional to HIF activity. These lowest concentrations were chosen since they provide the least effects on the general properties of the cells. Treatment of cells with plant extracts did not show any significant variation in the normoxic basal level of HIF activities (data not shown). Varying responses, however, were observed in the hypoxic samples (FIG. 2). Treatment with all of the plant extracts, except for Carica papaya, resulted in further activation of HIP activity, as evidenced from the negative values of the HIF inhibition. The level of activation however, varied among the different plant extracts. These variations did not show any obvious correlation to their viability at the low concentrations tested (FIG. 1A). Interestingly, the only candidate HIP Inhibitor found in this study, which was the Carica papaya extract, led to an almost 40% inhibition of HIP activity. This inhibition was almost comparable to cisplatin treatment, a known HIF inhibitor (Duyndam et al., 2007). This novel finding indicates the potential of Carica papaya extract as an agent to kill hypoxic cancer cells through inhibition of HIF activity.

Data presented in the foregoing study show specific cytotoxic effects of Carica papaya extract under hypoxic conditions as evidenced from a 3-fold reduction in $IC_{50}$ of hypoxic versus normoxic cells. This reduced $IC_{50}$ was achieved through specific inhibition of HIF activities.

Having established the effectiveness of Carica papaya extract to inhibit HIP activity, experiments were performed to determine the effect the age of the Carica papaya leaves on HIF inhibition. Leaves of the C. papaya were subjected to the methanolic extraction method to obtain crude leave extracts. Several batches of leave samples were originally obtained from different ages of plants from a farm that cultivates specific C. papaya varieties. The extracts were used in a HIF inhibition assay using the cell-based HIF assay system described above.

Figure 5:
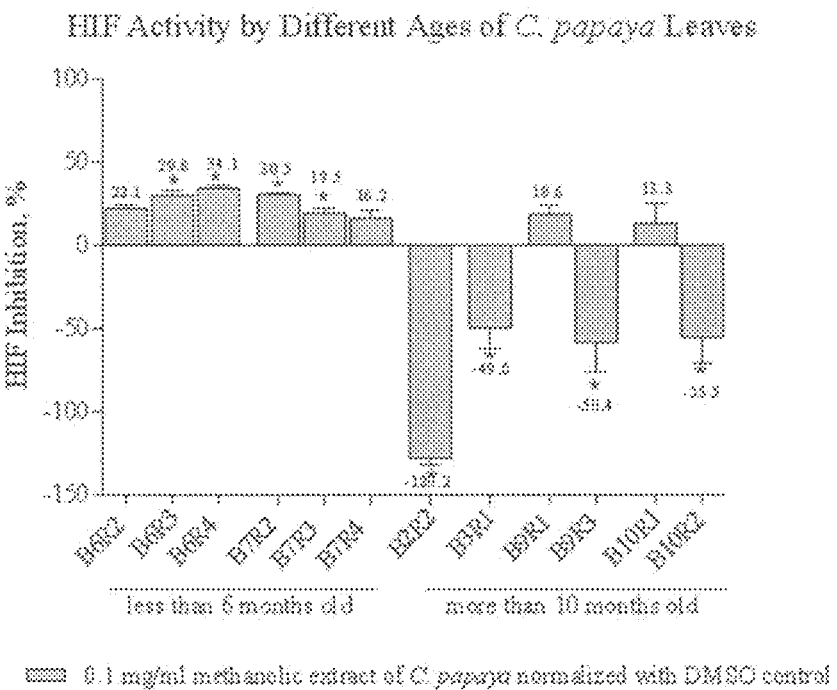
FIG. 5 shows the percent of HIF inhibition for leave crude extracts obtained from plants of age either six months or younger or older than six months, where negative inhibition value indicates activation of HIF, the symbol "*" denotes statistically significant difference (P<0.05) compared to the untreated control, B=Batch number, and R=Replicate.

HIF inhibitory activities were found to be dependent on the age of the plant from where the leaves were originally harvested. Referring to FIG. 5, statistically significant, replicable inhibition was seen in crude extract of leaves from plants ages 6 months and younger. An opposite effect, statistically significant activation of HIF, was noted when samples were obtained from plants that were older than 6 months of age.

Figure 6:
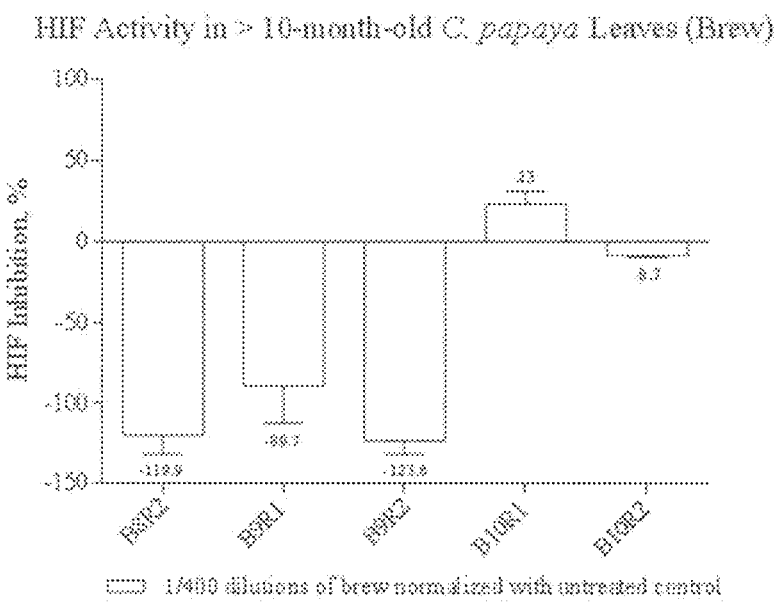
FIG. 6 shows the percentage of HIF inhibition with brew samples using prior art extraction procedures described in Morimoto et al. US patent Application No. 20080069907 on leaves obtained from plants older than 10 months from the date of germination of the seed, where negative inhibition value indicates activation of HIF, B=Batch number, and R=Replicate.

To compare the invention to the disclosure in prior art Morimoto et al. US patent Application No. 20080069907, HIF assays were performed using extraction procedures detailed in their patent application with plants that were older than 10 month. Referring to FIG. 6, results showed that a replicable inhibition of HIF was not seen. The HIF activity was instead increased, as evident from the negative values of HIF inhibition (the y-axis).

The alcohol used to extract the Carica papaya leaves was methanol. In general, one can use any of the monohydric, polyhydric, unsaturated aliphatic, or alicyclic alcohols, exemplified by methanol, ethanol, propanol, isopropanol, n-butanol, sec-butanol, isobutanol, tert-butanol, pentan-1-ol, 3-methylbutan-1-ol, 2-methylbutan-1-ol, 2,2-dimethylpropan-2-ol, pentan-3-ol, pentan-2-ol, 3-methylbutan-2-ol, 2-methylbutan-2-ol, ethane-1,2-diol, propane-1,2-diol, propane-1,2,3-triol, butane-1,2,3,4-tetraol, or pentane-1,2,3,4,5-pentol. The alcohol is preferably an acyclic alcohol having from 1 to five carbon atoms, most preferably methanol.

As described above, performed experiments using combinations of Carica papaya and cisplatin or chetomin led to an increase in cytotoxicity by 4-fold. Other chemotherapeutic agents can be used. More particularly, one can use in combination with the Carica papaya extract a chemotherapeutic agent selected from the group consisting of cisplatin, chetomin, methotrexate, trimetrexate, adriamycin, taxotere, 5-fluorouracil, vincristine, vinblastine, pamidronate disodium, anastrozole, exemestane, cyclophosphamide, epirubicin, toremifene, letrozole, trastuzumab, megestrol, tamoxifen, paclitaxel, docetaxel, capecitabine, goserelin acetate, 0-epi-1,25 dihydroxyvitamin D3,4-ipomeanol, 5-ethynyluracil, 9-dihydrotaxol, abiraterone, acivicin, aclarubicin, acodazole hydrochloride, acronine, acylfulvene, adecypenol, adozelesin, aldesleukin, all-tk antagonists, altretamine, ambamustine, ambomycin, ametantrone acetate, amidox, amifostine, aminoglutethimide, aminolevulinic acid, amrubicin, amsacrine, anagrelide, andrographolide, angiogenesis inhibitors, antagonist D, antagonist G, antarelix, anthramycin, anti-dorsalizing morphogenetic protein-1, antiestrogen, antineoplaston, antisense oligonucleotides, aphidicolin glycinate, apoptosis gene modulators, apoptosis regulators, apurinic acid, ARA-CDP-DL-PTBA, arginine deaminase, asparaginase, asperlin, asulacrine, atamestane, atrimustine, axinastatin 1, axinastatin 2, axinastatin 3, azacitidine, azasetron, azatoxin, azatyrosine, azetepa, azotomycin, baccatin III derivatives, balanol, batimastat, benzochlorins, benzodepa, benzoylstaurosporine, beta lactam derivatives, beta-alethine, betaclamycin B, betulinic acid, BFGF inhibitor, bicalutamide, bisantrene, bisantrene hydrochloride, bisaziridinylspermine, bisnafide, bisnafide dimesylate, bistratene A, bizelesin, bleomycin, bleomycin sulfate, BRC/ABL antagonists, breflate, brequinar sodium, bropirimine, budotitane, busulfan, buthionine sulfoximine, cactinomycin, calcipotriol, calphostin C, calusterone, camptothecin derivatives, canarypox IL-2, caracemide, carbetimer, carboplatin, carboxamide-amino-triazole, carboxyamidotriazole, carest M3, carmustine, earn 700, cartilage derived inhibitor, carubicin hydrochloride, carzelesin, casein kinase inhibitors, castanospermine, cecropin B, cedefingol, cetrorelix, chlorambucil, chlorins, chloroquinoxaline sulfonamide, cicaprost, cirolemycin, cis-porphyrin, cladribine, clomifene analogs, clotrimazole, collismycin A, collismycin B, combretastatin A4, combretastatin analog, conagenin, crambescidin 816, crisnatol, crisnatol mesylate, cryptophycin 8, cryptophycin A derivatives, curacin A, cyclopentanthraquinones, cycloplatam, cypemycin, cytarabine, cytarabine ocfosfate, cytotytic factor, cytostatin, dacarbazine, dacliximab, dactinomycin, daunorubicin hydrochloride, decitabine, dehydrodidemnin B, deslorelin, dexifosfamide, dexormaplatin, dexrazoxane, dexverapamil, dezaguanine, dezaguanine mesylate, diaziquone, didemnin B, didox, diethylnorspermine, dihydro-5-azacytidine, dioxamycin, diphenyl spiromustine, docosanol, dolasetron, doxifluridine, doxorubicin hydrochloride, droloxifene, droloxifene citrate, dromostanolone propionate, dronabinol, duazomycin, duocarmycin SA, ebselen, ecomustine, edatrexate, edelfosine, edrecolomab, eflomithine, eflornithine hydrochloride, elemene, elsamitrucin, emitefur, enloplatin, enpromate, epipropidine, epirubicin hydrochloride, episteride, erbulozole, erythrocyte gene therapy vector system, esorubicin hydrochloride, estramustine, estramustine analog, estramustine phosphate sodium, estrogen agonists, estrogen antagonists, etanidazole, etoposide, etoposide phosphate, etoprine, fadrozole, fadrozole hydrochloride, fazarabine, fenretinide, filgrastim, finasteride, flavopiridol, flezelastine, floxuridine, fluasterone, fludarabine, fludarabine phosphate, fluorodaunorunicin hydrochloride, fluorocitabine, forfenimex, formestane, fosquidone, fostriecin, fostriecin sodium, fotemustine, gadolinium texaphyrin, gallium nitrate, galocitabine, ganirelix, gelatinase inhibitors, gemcitabine, gemcitabine hydrochloride, glutathione inhibitors, hepsulfam, heregulin, hexamethylene bisacetamide, hydroxyurea, hypericin, ibandronic acid, idarubicin, idarubicin hydrochloride, idoxifene, idramantone, ifosfamide, ilmofosine, ilomastat, imidazoacridones, imiquimod, immunostimulant peptides, insulin-like growth factor-1 receptor inhibitor, interferon agonists, interferon alpha-2A, interferon alpha-2B, interferon alpha-N1, interferon alpha-N3, interferon beta-IA, interferon gamma-IB, interferons, interleukins, iobenguane, iododoxorubicin, iproplatin, irinotecan, irinotecan hydrochloride, iroplact, irsogladine, isobengazole, iso-homohalicondrin B, itasetron, jasplakinolide, kahalalide F, lamellarin-N triacetate, lanrmeotide, lanreotide acetate, leinamycin, lenograstim, lentinan sulfate, leptolstatin, leukemia inhibiting factor, leukocyte alpha interferon, leuprolide acetate, leuprolide/estrogen/progesterone, leuprorelin, levamisole, liarozole, liarozole hydrochloride, linear polyamine analog, lipophilic disaccharide peptide, lipophilic platinum compounds, lissoclinamide 7, lobaplatin, lombricine, lometrexol, lometrexol sodium, lomustine, lonidamine, losoxantrone, losoxantrone hydrochloride, lovastatin, loxoribine, lurtotecan, lutetium texaphyrin, lysofylline, lytic peptides, maitansine, mannostatin A, marimastat, masoprocol, maspin, matrilysin inhibitors, matrix metalloproteinase inhibitors, maytansine, mechlorethamine hydrochloride, megestrol acetate, melengestrol acetate, melphalan, menogaril, merbarone, mercaptopurine, meterelin, methioninase, methotrexate sodium, metoclopramide, metoprine, meturedepa, microalgal protein kinase C inhibitors, MIF inhibitor, mifepristone, miltefosine, mirimostim, mismatched double stranded RNA, mitindomide, mitocarcin, mitocromin, mitogillin, mitoguazone, mitolactol, mitomalcin, mitomycin, mitomycin analogs, mitonafide, mitosper, mitotane, mitotoxin fibroblast growth factor-saporin, mitoxantrone, mitoxantrone hydrochloride, mofarotene, molgramostim, monoclonal antibody, human chorionic gonadotrophin, monophosphoryl lipid a/myobacterium cell wall SK, mopidamol, multiple drug resistance gene inhibitor, multiple tumor suppressor 1-based therapy, mustard anticancer agent, mycaperoxide B, mycobacterial cell wall extract, mycophenolic acid, myriaporone, n-acetyldinaline, nafarelin, nagrestip, naloxone/pentazocine, napavin, naphterpin, nartograstim, nedaplatin, nemorubicin, neridronic acid, neutral endopeptidase, nilutamide, nisamycin, nitric oxide modulators, nitroxide antioxidant, nitrullyn, nocodazol, nogalamycin, n-substituted benzamides, 06-benzylguanine, octreotide, okicenone, oligonucleotides, onapristone, ondansetron, oracin, oral cytokine inducer, ormaplatin, osaterone, oxaliplatin, oxaunomycin, oxisuran, paclitaxel analogs, paclitaxel derivatives, palauamine, palmitoylrhizoxin, pamidronic acid, panaxytriol, panomifene, parabactin, pazelliptine, pegaspargase, peldesine, peliomycin, pentamustine, pentosan polysulfate sodium, pentostatin, pentrozole, peplomycin sulfate, perflubron, perfosfamide, perillyl alcohol, phenazinomycin, phenylacetate, phosphatase inhibitors, picibanil, pilocarpine hydrochloride, pipobroman, piposulfan, pirarubicin, piritrexim, piroxantrone hydrochloride, placetin A, placetin B, plasminogen activator inhibitor, platinum complex, platinum compounds, platinum-triamine complex, plicamycin, plomestane, porfimer sodium, porfiromycin, prednimustine, procarbazine hydrochloride, propyl bis-acridone, prostaglandin J2, prostatic carcinoma antiandrogen, proteasome inhibitors, protein A-based immune modulator, protein kinase C inhibitor, protein tyrosine phosphatase inhibitors, purine nucleoside phosphorylase inhibitors, puromycin, puromycin hydrochloride, purpurins, pyrazofurin, pyrazoloacridine, pyridoxylated hemoglobin polyoxyethylene conjugate, RAF antagonists, raltitrexed, ramosetron, RAS farnesyl protein transferase inhibitors, RAS inhibitors, RAS-GAP inhibitor, retelliptine demethylated, rhenium RE 186 etidronate, rhizoxin, riboprine, ribozymes, RII retinamide, RNAi, rogletimide, rohitukine, romurtide, roquinimex, rubiginone B1, ruboxyl, safingol, safingol hydrochloride, saintopin, sarcnu, sarcophytol A, sargramostim, SDII mimetics, semustine, senescence derived inhibitor I, sense oligonucleotides, signal transduction inhibitors, signal transduction modulators, simtrazene, single chain antigen binding protein, sizofuran, sobuzoxane, sodium borocaptate, sodium phenylacetate, solverol, somatomedin binding protein, sonermin, sparfosate sodium, sparfosic acid, sparsomycin, spicamycin D, spirogermanium hydrochloride, spiromustine, spiroplatin, splenopentin, spongistatin 1, squalamine, stem cell inhibitor, stem-cell division inhibitors, stipiamide, streptonigrin, streptozocin, stromelysin inhibitors, sulfinosine, sulofenur, superactive vasoactive intestinal peptide antagonist, suradista, suramin, swainsonine, synthetic glycosaminoglycans, talisomycin, tallimustine, tamoxifen methiodide, tauromustine, tazarotene, tecogalan sodium, tegafur, tellurapyrylium, telomerase inhibitors, teloxantrone hydrochloride, temoporfin, temozolomide, teniposide, teroxirone, testolactone, tetrachlorodecaoxide, tetrazomine, thaliblastine, thalidomide, thiamiprine, thiocoraline, thioguanine, thiotepa, thrombopoictin, thrombopoietin mimetic, thymalfasin, thymopoietin receptor agonist, thymotrinan, thyroid stimulating hormone, tiazofurin, tin ethyl etiopurpurin, tirapazamine, titanocene dichloride, topotecan hydrochloride, topsentin, toremifene citrate, totipotent stem cell factor, translation inhibitors, trestolone acetate, tretinoin, triacetyluridine, triciribine, triciribine phosphate, trimetrexate, trimetrexate glucuronate, triptorelin, tropisetron, tubulozole hydrochloride, turosteride, tyrosine kinase inhibitors, tyrphostins, UBC inhibitors, ubenimex, uracil mustard, uredepa, urogenital sinus-derived growth inhibitory factor, urokinase receptor antagonists, vapreotide, variolin B, velaresol, veramine, verdins, verteporfin, vinblastine sulfate, vincristine sulfate, vindesine, vindesine sulfate, vinepidine sulfate, vinglycinate sulfate, vinleurosine sulfate, vinorelbine, vinorelbine tartrate, vinrosidine sulfate, vinxaltine, vinzolidine sulfate, vitaxin, vorozole, zanoterone, zeniplatin, zilascorb, zinostatin, zinostatin stimalamer, and zorubicin hydrochloride, as well as salts, homologs, analogs, derivatives, enantiomers and/or functionally equivalent compositions thereof.

Although the present invention has been described in connection with the preferred embodiments, it is to be understood that modifications and variations may be utilized without departing from the principles and scope of the invention, as those skilled in the art will readily understand.

REFERENCES

Ahmad N, Fazal H, Ayazd M, Abbasi M H, Mohammad I, Fazale L. Dengue fever treatment with *Carica papaya* leaves extracts, Asian Pac J Trop Biomed. 2011, 1(4): 330-333.

Brown, J. M., 2000. Hypoxic cytotoxic agents: a new approach to cancer chemotherapy. Drug Resistance Update 3, 7-13.

Canini A, Alesiani D, D'Arcangelo G, Tagliatesta P. Gas chromatography-mass spectrometry analysis of phenolic compounds from *Carica papaya* L. leaf. J Food Comp Anal. 2007, 20(7): 584-590.

Devehat, L. L., Bakhtiar, A., Bezivin, C., Amoros, M., Boustie, J., 2002. Antiviral and cytotoxic activities of some Indonesian plants. Fitoterapia 73, 400-405.

Duyndam., M. C., Berkel, M. P., Dorsman, J. C., Rockx, D. A., Pinedo, H. M., Boven, E., 2007. Cisplatin and doxorubicin repress vascular endothelial growth factor expression and differentially down-regulate hypoxia-inducible factor I activity in human ovarian cancer cells. Biochemical Pharmacology 74, 191-201.

Er, H. M., Cheng, E. H., Radhakrishnan, A. K., 2007. Anti-proliferative and mutagenic activities of *aqueous* and methanol extracts of leaves from *Pereskia bleo* (Kunth) DC (Cactaceae). Journal of Ethnopharmacology 113, 448-456.

Graziose, R., Lila, M. A., Raskin. I., 2010. Merging traditional Chinese medicine with modern drug discovery technologies to find novel drugs and functional foods. Current Drug Discovery Technologies 7, 2-12.

Hsu, C. L., Hong, B. H., Yu, Y. S., Yen, G. C., 2010. Antioxidant and anti-inflammatory effects of *Orthosiphon aristatus* and its bioactive compounds. Journal of Agricultural and Food Chemistry 58, 2150-2156.

Huang, H. C., Liaw, C. C., Zhang, L J., Ho, H. U., Kuo, L. M., Shen, Y. C., Kuo, Y. H., 2008. Triterpenoidal saponins from *Hydrocotyle sibthorpioides*. Phytochemistry 69, 1597-1603.

Jamal, M. H., Ch'ng, W. C., Yusoff, K., Shafee, N., 2012. Reduced Newcastle disease virus-induced oncolysis in a subpopulation of cisplatin-resistant MCF7 cells is associated with survivin stabilization. Cancer Cell International 12, 35.

Kaluz, S., Milota Kaluzova, M., Stanbridge, E J., 2008. Rational design of minimal hypoxia-inducible enhancers. Biochemical and Biophysical Research Communications 370, 613-618.

Lu J, Zhang K, Chen S, Wen W. Grape seed extract inhibits VEGF expression via reducing HIF-1α protein expression. Carcinogenesis. 2009, 30(4): 636-644.

Mahmood A A, Sidik K, Salmah I. Wound healing activity of *Carica papaya* L. aqueous leaf extract in rats. Intern J Mol Med Adv Sc. 2005, 1(4): 398-401.

Malek, S. N. A., Shin, S. K., Wahab, N. A., Yaacob, H., 2009. Cytotoxic components of *Pereskia bleo* (Kunth) DC. (Cactaceae) leaves. Molecules 14, 1713-1724.

Miyata T, Takizawa S, van Ypersele de Strihou C. Intracellular sensors for oxygen and oxidative stress: novel therapeutic targets. Am J Physiol Cell Physiol. 2011, 300(2): C226-31.

Morimoto C, Dang N H. Compositions for cancer prevention, treatment, or amelioration comprising *papaya* extract. US Patent Application #20080069907.

Nagle D G, Zhou Y D. Marine natural products as inhibitors of hypoxic signaling in tumors. Phytochem Rev. 2009, 8(2): 415-429.

Otsuki, N., Dang, N. H., Kumagai, E., Kondo, A., Iwata, S., Morimoto, C., 2010. *Aqueous* extract of *Carica papaya* leaves exhibits anti-tumor activity and immunomodulatory effects. Journal of Ethnopharmacology 127, 760-767.

Sanchez E, Li M. Wang C, Nichols C M, Li J, Chen H, Berenson J R. Anti-myeloma effects of the novel anthracycline derivative INNO-206. Clin Cancer Res. 2012, 15; 18(14):3856-67.

Semenza, G. L., 2011. Hypoxia. Cross talk between oxygen sensing and the cell cycle machinery. American Journal of Physiology—Cell Physiology 301, C550-552.

Seol J W, Lee H B, Lee Y J, Lee Y H, Kang H S, Kim I S, Kim N S, Park S Y. Hypoxic resistance to articular chondrocyte apoptosis-a possible mechanism of maintaining homeostasis of normal articular cartilage. FEBS J. 2009, 276(24):7375-85.

Shafee, N., Kaluz, K, Ru, N., Stanbridge, E. J., 2009. PI3K/Akt activity has variable cell-specific effects on expression of HIF target genes, CA9 and VEGF, in human cancer cell lines. Cancer Letters 282, 109-115.

Shafee N, Stanbridge E J, Yusoff K, Liew S Y, Hypoxia inducible factor (HIF) activity reporter cell line. Malaysian Patent Application #: PI 2012003492.

Solecki, R., Shanidar, I. V., 1975. A Neanderthal flower burial in northern Iraq. Science 190, 880-881.

Song, X., Liu, X., Chi, W., Liu, Y., Wei. L., Wang, X., Yu, J., 2006. Hypoxia-induced resistance to cisplatin and doxorubicin in non-small cell lung cancer is inhibited by silencing of HIF-la gene. Cancer Chemotherapy and Pharmacology 58, 776-784.

Tan, C., deNoronha, R. G., Roecker, A. J., Pyrzynska, B., Khwaja, F., Zhang, Z., Zhang, H., Teng, Q., Nicholson, A. C., Giannakakou, P., Zhou, W., Olson, J. J., Pereira, M. M., Nicolaou, K. C., Van Meir, E. G., 2005. Identification of a novel small-molecule inhibitor of the hypoxia-inducible factor 1 pathway. Cancer Research 65, 605-612.

Xia Y, Choi H K, Lee K. Recent advances in hypoxia-inducible factor (HIF)-1 inhibitors. European J Med Chem. 2012, 49:24-40.

Yamaguchi T, Sasaki M, Itoh K. Bortezomib-induced pneumonitis during bortezomib retreatment in multiple myeloma. Jpn J Clin Oncol. 2012, 42(7):637-9.

Zahra, A. A., Kadir, F. A., Mahmood, A. A., Al hadi, A. A., Suzy, S. M., Sabri, S. Z., Latif, I. I., Ketuly, K. A., 2011.

Acute toxicity study and wound healing potential of *Gynura procumbens* leaf extract in rats. Journal of Medicinal Plants Research 5, 2551-2558.

Zhang Q, Tang X, Lu Q, Zhang Z, Rao J, Le A D. Green tea extract and (−)-epigallocatechin-3-gallate inhibit hypoxia- and serum-induced HIF-1 alpha protein accumulation and VEGF expression in human cervical carcinoma and hepatoma cells. Mol Cancer Ther. 2006, 5(5): 1227-38.

The invention claimed is:

1. A pharmacon for treating a solid hypoxic tumor having hypoxia-inducible factors, comprising a therapeutically acceptable and effective amount of an alcohol extract from *Carica papaya* leaves obtained from a plant of age six months and younger from the date of germination of the seed, the extract being contained in a liposome or in a polymer release system, or suspended as a colloid in a liquid.

2. The pharmacon of claim 1 in which the alcohol extract is a monohydric, polyhydric, unsaturated aliphatic, or alicyclic alcohol extract.

3. The pharmacon of claim 2 in which the extract is a methanol extract.

4. A pharmacon for treating a solid hypoxic tumor having hypoxia-inducible factors, comprising:
   (a) a therapeutically acceptable and effective amount of an alcohol extract from *Carica papaya* leaves obtained from a plant of age six months and younger from the date of germination of the seed, and
   (b) a therapeutically acceptable and effective amount of a chemotherapeutic agent other than said alcohol extract, wherein the pharmacon is contained within a package.

5. The pharmacon of claim 4 wherein the chemotherapeutic agent is cisplatin.

6. The pharmacon of claim 4 wherein the chemotherapeutic agent is chetomin.

* * * * *